United States Patent [19]

Sommer

[11] Patent Number: 4,692,530

[45] Date of Patent: Sep. 8, 1987

[54] CHEMICAL AGENTS

[75] Inventor: Harold Z. Sommer, Havre de Grace, Md.

[73] Assignee: The United States of America as represented by the Secretary of the Army, Washington, D.C.

[21] Appl. No.: 624,649

[22] Filed: Mar. 7, 1967

[51] Int. Cl.[4] .................... C07D 213/69; C07C 125/06

[52] U.S. Cl. ........................................ 546/261; 560/25

[58] Field of Search ................. 260/247.2 A, 294.7 E, 260/296, 482 B, 558 A; 167/30 G, 47; 424/248, 267, 274, 300; 560/25; 546/261

[56] References Cited

U.S. PATENT DOCUMENTS

| | | | |
|---|---|---|---|
| 3,188,955 | 6/1965 | Brown | 102/24 |
| 3,251,839 | 5/1966 | Downes et al. | 260/247.2 X |
| 3,309,376 | 3/1967 | Haas et al. | 260/296 |
| 3,940,363 | 2/1976 | Murayama et al. | 546/261 |

FOREIGN PATENT DOCUMENTS

| | | | |
|---|---|---|---|
| 782789 | 9/1957 | United Kingdom | 260/482 B |

*Primary Examiner*—John F. Terapane
*Assistant Examiner*—Eric Jorgensen
*Attorney, Agent, or Firm*—Anthony T. Lane; Harold H. Card, Jr.

[57] ABSTRACT

New toxic chemical compounds having the generic formula:

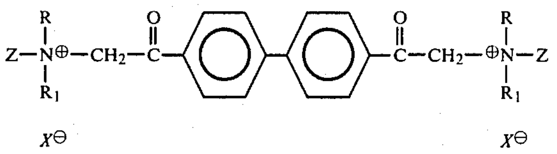

and utility and method of preparation thereof wherein X is one equivalent of an anion selected from the group consisting of halide, hydrogen sulfate, nitrate, hydrogen oxalate and perchlorate and R and $R_1$ are methyl while Z is a radical selected from 3-dimethylcarbamoxyphenyl, 2-dimethylcarbamoxybenzyl or 3-dimethyl carbamoxy-α-picolinyl.

3 Claims, No Drawings

CHEMICAL AGENTS

This invention relates to the synthesis of new toxic chemical compounds which are useful as chemical warfare agents. More particularly, our invention is concerned with novel compounds produced in a quaternization reaction.

These chemical agents act mostly on the peripheral autonomic cholinergic nervous system which includes the motor nerves, all preganglionic fibers and the postganglionic parasympathetic fibers, ganglia, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers, they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures, different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influence association and hydration and may considerably change the solubilities in physiological media. In bis-quaternary and poly-quaternary compounds, the distance between the electric charges must be considered. These factors among others govern the rate and reversibility of the chemical reactions involved that determine the final physiological responses.

The chemical agents which constitute this invention interfere with the normal process of neuromuscular impulse transmission and thus disrupt the propagation of impulses from nerves to muscles. I have also found these compounds to be extremely toxic at relatively low dose levels in various animals.

The object of this invention is to synthesize new lethal agents in high yields wherein said products are well suited for industrial scale manufacture.

Other objects of and uses for the invention will appear in the following detailed description thereof.

My compounds are useful as chemical warfare agents. They have an extremely high lethal activity.

My compounds may be employed in any munition suitable for handling a relatively non-volatile toxic agent such as bombs, shells, spray tanks, rockets, missiles, aerosol generators, and others.

In accordance with my invention, α,α′-dibromo-4,4′-biacetophenone in a solvent such as alcohol or tetrahydrofuran was mixed with an aminocarbamate, such as 3-dimethylcarbamoxydimethylaniline. The mixture was refluxed for several hours during which time a precipitate formed. The precipitate was washed with a solvent such as ethanol purified and collected.

The precipitate thus obtained constitutes new compounds of the present invention which may be represented by the following generic formula:

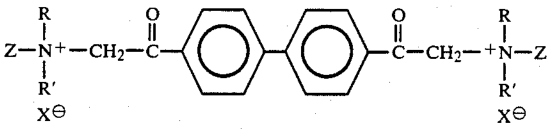

where X is one equivalent of a monovalent or polyvalent anion, R and R′ are methyl groups, and where Z is a radical such as:

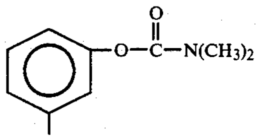

3-dimethylcarbamoxyphenyl

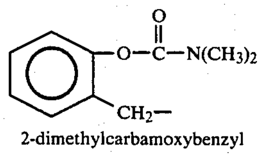

2-dimethylcarbamoxybenzyl

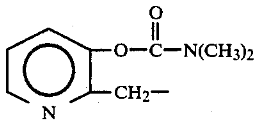

3-dimethylcarbamoxy-α-picolinyl with the provision that when Z is a 3-dimethylcarbamoxy-α-picolinyl group, NRR′ are combined to form the following radicals:

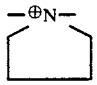

PYRROLIDINIO

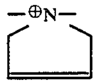

3-PYRROLINIO

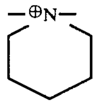

PIPERDINIO

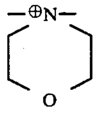

MORPHOLINIO

The procedure used for the preparation of the new toxic materials is schematically shown below:

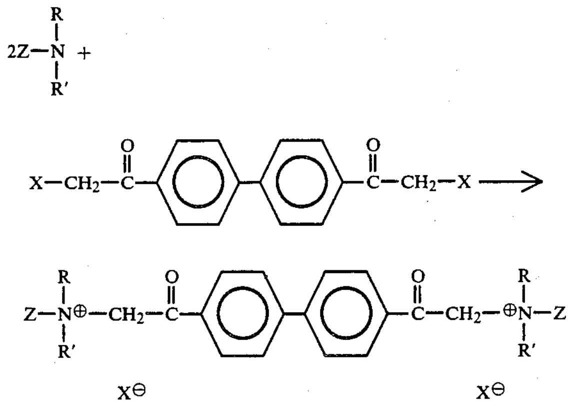

where X is any halide radical, X⊖ is the corresponding halide anion, preferably chlorine or bromine, and R,R' and Z as defined above.

In the above reaction, we have found that the incoming dihaloacetophenone adds to the nitrogen atoms in the aforementioned amines and in those instances with two tertiary nitrogens in a single molecule we have found that the addition occurs preferentially at the nitrogens of the alicyclic moieties because of their higher basicities. If compounds are desired in which X is other than a halide ion, the above quaternary compounds are treated with the desired acid by a simple ion exchange reaction as set forth below.

The aminocarbamates, with the exception of 3-dimethylcarbamoxydimethylaniline which was obtained by distilling the readily available corresponding methobromide known as prostigmine under reduced pressure, were prepared by the Mannich reaction on phenol or 3-pyridol with the desired secondary amines and subsequent carbamoylation of the resultant Mannich bases with dimethylcarbamoyl chloride, schematically shown below:

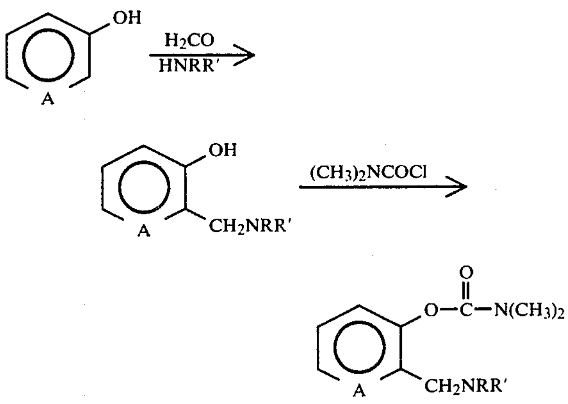

where A represents a carbon or a nitrogen atom, R and R' are methyl groups, and NRR' combined represent pyrrolidinyl, 3-pyrrolinyl, piperidinyl, and morpholinyl groups.

EXAMPLE 1

A mixture of 2.2 g of 3-dimethylcarbamoxydimethylaniline, 1.18 g of α,α'-dibromo-4,4'-biacetophenone, 60 ml of ethanol, and 120 ml of water was refluxed for 30 hours. The solvents were evaporated under reduced pressure of about 50 mm. The oily residue was dissolved in 30 ml of hot ethanol, the solution stirred with 1 g of decolorizing charcoal for 15 minutes and then filtered. Ethyl acetate was added to the filtrate and the mixture was refrigerated overnight. The light yellow precipitate that formed was collected on a filter. The product, bis{α-[(3-dimethylcarbamoxyphenyl)methylamino]}-4,4'-biacetophenone dimethobromide, contained 1 mole of water after being dried in vacuo over phosphorus pentoxide for 20 hours; the melting point was found to be 150°-152° C.

Anal. Calc. for $C_{38}H_{44}Br_2N_4O_6.1H_2O$: C, 54.95; H, 5.55; O, 13.5; Br, 19.3. Found: C, 55.3; H, 5.7; O, 13.2; Br, 18.9.

| Toxicity I.V. $LD_{50}$ | |
|---|---|
| Rabbits | Mice |
| 0.028 mg/kg | 0.018 mg/kg |

EXAMPLE 2

A mixture of 114 g of 3-pyridol, 91 g of pyrrolidine, 107 g of a 37% aqueous formaldehyde solution, and 200 ml of water was heated on a steam bath for 3½ hours, after which time the reaction mixture was distilled under reduced pressure. The fraction boiling between 118°-140° C. at 3.5 mm pressure was collected. On redistillation of this fraction, 130 g of 2-(N-pyrrolidinomethyl)pyridine boiling between 100°-110° C., at 1.5-2 mm pressure was obtained. Pyridine (128 ml) and 82 g of dimethylcarbamoyl chloride were then added to the Mannich base and the mixture was refluxed for 1½ hours. After the reaction mixture cooled to room temperature, it was poured onto 200 g of ice. The resultant solution was made basic by the addition of sodium carbonate and extracted with chloroform. The chloroform extract was dried over anhydrous sodium sulfate and distilled under reduced pressure. The fraction distilling between 90°-130° C. at 1.6 mm presssure was collected. Redistillation of this fraction yielded 49 g of 3-dimethylcarbamoxy-2-(N-pyrrolidinomethyl)pyridine boiling between 117° and 120° C. at 0.08 mm pressure.

A mixture of 2.0 g of the above 3-dimethylcarbamoxy-2-(N-pyrrolidinomethyl)pyridine and 1.6 g of α,α'-dibromo-4,4'-biacetophenone in 50 ml of tetrahydrofuran was refluxed for two hours and then cooled to room temperature. The precipitate that formed was purified by dissolving it in ethanol and stirring the solution with charcoal. After the charcoal was removed by filtration, ether was added. The crystalline material that formed was vacuum dried over phosphorus pentoxide for eight hours at room temperature. The product, bis-{α-[(3-dimethylcarbamoxy-α-picolinyl)pyrrolidinio]}-4,4'-biacetophenone dibromide (1.5 g) was obtained as the monohydrate, melting at 134°-138° C. with decomposition. Anal. Calc. for $C_{42}H_{50}Br_2N_6O_6.H_2O$: C, 55.25; H, 5.7; O, 12.3. Found: C, 55.4; H, 5.5; O, 12.7.

| Toxicity IV. $LD_{50}$ | |
|---|---|
| Rabbits | Mice |
| 0.010 mg/kg | 0.022 mg/kg |

The compounds that are representative of our invention are listed below by name and chemical structure.

Bis{α-[(3-dimethylcarbamoxyphenyl)methylamino]}-4,4'-biacetophenone dimethobromide.

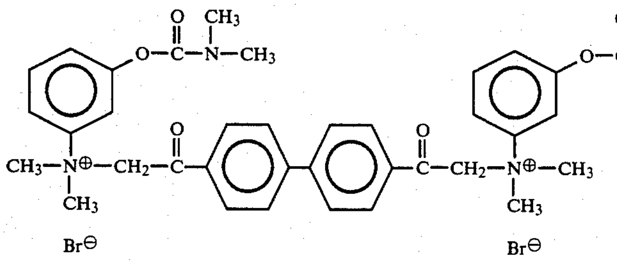

Bis{α-[(2-dimethylcarbamoxybenzyl)methylamino]}-4,4'-biacetophenone dimethobromide.

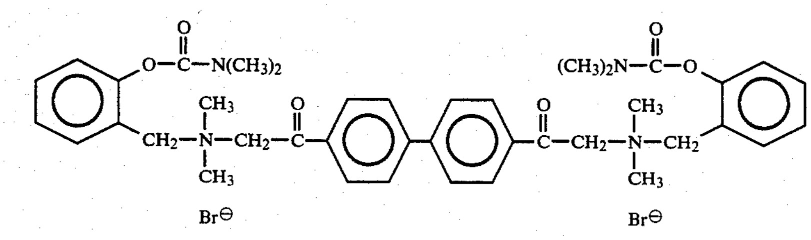

Bis{α-[(3-dimethylcarbamoxy-α-picolinyl pyrrolidino]}4,4'-biacetophenone dibromide.

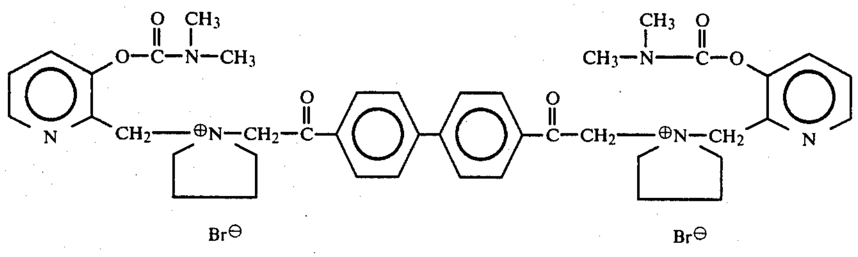

We have shown preferred compounds in which the anion is limited to a halogen, in particular the bromide, since the α,α'-dibromo-4,4'-biacetophenones are readily available and are good quaternizing agents. In general, however, it is only necessary that the anions merely have to meet the requirement of being capable of forming a stable salt with the quaternary nitrogens. Thus, the halogen ion can be exchanged with other anions of a relatively strong monovalent or polyvalent acids by conventional methods. For example, if X is a bromide in the bis-quaternary compound, it can be treated with a basic ion exchange resin or mixed with silver oxide and subsequently the desired acid is added. In like manner, the hydrogen sulfate, nitrate, hydrogen oxalate, perchlorate salts may be prepared. Represenative examples of these additional monovalent or polyvalent bisquaternary compounds are:

Bis{α-[(3-dimethylcarbamoxy-α-picolinyl)pyrrolidinio]}-4,4'-biacetophenone di(hydrogensulfate).

Bis{α-[(3-dimethylcarbamoxy-α-picolinyl)3-pyrrolino]}-4,4'-biacetophenone dinitrate.

Bis{α-[(3-dimethylcarbamoxy-α-picolinyl)piperdinio]}-4,4'-biacetophenone di(hydrogenoxalate).

Bis{α-[(3-dimethylcarbamoxy-α-picolinyl)morpholinio}-4,4'-biacetophenone diperchlorate.

I claim:

1. Chemical compound having the formula:

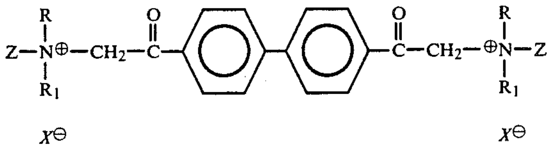

where X is one equivalent of an anion selected from the group consisting of monovalent and polyvalent, said anions being selected from the group consisting of halide, hydrogen sulfate, nitrate, hydrogen oxalate, and perchlorate, R and $R_1$ are methyl groups and Z is a radical selected from the group consisting of 3-dimethylcarbamoxyphenyl, 2-dimethylcarbamoxybenzyl, and 3-dimethylcarbamoxy-α-picolinyl.

2. The compound of claim 1 wherein Z is 3-dimethylcarbamoxy-α-picolinyl.

3. A method of producing bis{α-[(3-dimethylcarbamoxyphenyl)methylamino]}-4,4'-biacetophenone dimethobromide comprising the steps of refluxing for about twenty hours a mixture of 2.2 grams of 3-dimethylcarbamoxydimethylaniline, 1.18 grams of α,α'-dibromo-4,4'-biacetophenone, 60 ml. of ethanol, and 120 ml. of water; evaporating the solvents under a reduced pressure of about 50 mm.; dissolving the oily residue in 30 ml. of hot ethanol; adding 1 gram of decolorizing charcoal to said oily residue solution and stirring for about 15 minutes; filtering said oily residue solution; adding ethyl acetate to the filtrate of said only residue solution; refrigerating said filtrate plus ethyl acetate overnight to form a yellow precipitate; and drying said precipitate in vacuo over phosphorus pentoxide for about twenty hours.

* * * * *